United States Patent [19]

Geller et al.

[11] Patent Number: 5,002,940

[45] Date of Patent: Mar. 26, 1991

[54] SOLID DRUG FORMULATIONS AND STABLE SUSPENSIONS

[75] Inventors: Leo Geller, Riehen; Peter Glanzmann, Basel, both of Switzerland

[73] Assignee: Ciba-Geigy Corporation, Ardsley, N.Y.

[21] Appl. No.: 792,077

[22] Filed: Oct. 28, 1985

[30] Foreign Application Priority Data

Nov. 6, 1984 [CH] Switzerland .......................... 5305/84

[51] Int. Cl.$^5$ .................... A61K 31/565; A61K 31/74
[52] U.S. Cl. ...................................... 514/178; 424/78
[58] Field of Search ............... 514/178, 78; 260/397.4; 424/78

[56] References Cited

U.S. PATENT DOCUMENTS

| | | | |
|---|---|---|---|
| 4,235,893 | 11/1980 | Brodie et al. | 514/178 |
| 4,309,423 | 1/1982 | Biollaz | 260/397.4 |
| 4,391,755 | 7/1983 | Wang et al. | 260/397.45 |

FOREIGN PATENT DOCUMENTS

| | | |
|---|---|---|
| 95751 | 12/1983 | European Pat. Off. . |
| 117811 | 9/1984 | European Pat. Off. . |
| 3339295 | 5/1984 | Fed. Rep. of Germany . |
| 6940803 | 8/1971 | France . |

OTHER PUBLICATIONS

Chemical Abstracts, vol. 105 (1986), #102601A; Geller et al.

*Primary Examiner*—Shep K. Rose
*Attorney, Agent, or Firm*—Irving M. Fishman; JoAnn Villamizar

[57] ABSTRACT

The invention relates to solid drug formulations obtainable by lyophilization for the preparation of stable suspensions and to the stable suspensions themselves, which formulations contain 4-hydroxy- or 4-acyloxy-4-androstene-3,17-diones.

10 Claims, No Drawings

SOLID DRUG FORMULATIONS AND STABLE SUSPENSIONS

The present invention relates to solid drug formulations for the preparation of stable suspensions which contain 4-hydroxy- or 4-acyloxy-4-androstene-3,17-diones as active ingredients, and to the preparation thereof.

According to H. Sucker, P. Fuchs and P. Speiser, Pharmazeutische Technologie (1978), Verlag G. Thieme Stuttgart, page 616, aqueous suspensions of steroid compounds usually contain, as suspension excipients, for example a wetting agent in low concentration, e.g. from 0.1 to 0.5 mg/ml of polysorbate or 0.15 mg/ml of dioctyl sodium sulfosuccinate, a protective colloid such as sodium carboxymethylcellulose or methyl cellulose, and a peptisator, e.g. a phosphate buffer. It is common knowledge, however, that these excipients must be added within very narrow limits to ensure the physical stability of the suspension. If the formulation is not optimally constituted within these narrow limits, there is the danger that either the suspended drug will crystallise or it will prematurely settle and no longer form a homogeneous suspension after a time by shaking, and will no longer meet the ideal requirements set forth in Remington's Pharmaceutical Sciences (1980) (A. Osol), page 1457.

There is a genuine need to provide a stable aqueous suspension without the shortcomings referred to above. Furthermore, there is a need in medicine to provide suspensions as drop formulations, as often it is easier to persuade patients to take drops than capsules or tablets. In particular, injectable suspensions can be administered to the patient in any condition.

Surprisingly, it has been possible to obtain, by lyophilisation, solid drug formulations for the preparation of stable suspensions and stable suspensions themselves, in particular injection suspensions, which contain 4-hydroxy- or 4-acyloxy-4-androstene-3,17-diones as active ingredients, and containing as wetting agent and as agent for raising the viscosity of the suspending agent, a combination consisting of at least one phospholipid and at least one polyethylene glycol in a ratio of 1:1 to 1:10.

Surprisingly, it has been found that the ratio of the combination of phospholipid/polyethylene glycol is of great importance for the solid drug formulations obtainable by lyophilisation for the preparation of stable suspensions.

The ratio of the combination of phospholipid and polyethylene glycol is preferably in the range from 1:1 to 1:5.0, most preferably from 1:1 to 1:3.0.

Suitable phospholipids for use as wetting agents in combination with polyethylene glycol are mixtures of phosphatidyl choline, phosphatidyl ethanolamine, N-acylphosphatidyl ethanolamine or phosphatidyl inisotol, especially phospholipids containing 30–98% of phosphatidyl choline.

The following commercial products may for example be used:

| Concentration of phosphatidyl choline | Registered trademark |
| --- | --- |
| c. 45% | Epikuron 145 ® |
| | Lipoid S45 ® |
| 80–85% | Epikuron 170 ® |
| | Lipoid E80 ® |
| 90–98% | Epikuron 200 ® |
| | Lipoid S100 ® |

Combinations of different phospholipids have proved particularly suitable.

A salient feature of the invention resides in the choice of polyethylene glycol, as it has been found that the desired stabilisation of the suspension can only be attained if preferably one polyethylene glycol of high molecular weight is employed. Particularly good results are obtained by using solely solid polyethylene glycols having a molecular weight from 1000 to 6000. It is preferred to use polyethylene glycols having a molecular weight from 3000 to 4000 for the preparation of suspensions which contain 4-hydroxy-4-androstene-3,17-dione. The use of these solid polyethylene glycols results in a slight increase in viscosity of the suspension vehicle, which leads in turn to an improvement in the suspending power of the active ingredient. Further, these polyethylene glycols act as builders in the subsequent lyophilisation. Solid polyethylene glycols of the indicated molecular weight are commercially available under various trademarks, for example Polyglycol or Carbowax 1000 ®, 1500 ®, 3000 ®, 4000 ® or 6000 ®.

To the skilled person it was unexpected that, in addition to the above mentioned combination of phospholipid/polyethylene glycol, the average molecular weight has such a pronounced influence on the physical stability of the suspension.

As already mentioned, the combination of the two excipients results in a suspension vehicle of slightly increased viscosity in which the drug can be distributed homogeneously in varying crystal structure and concentration. A particular advantage of this suspension vehicle is that resultant suspensions can be lyophilised, whereby any, i.e. all, stability problems can be reduced to a minimum. Lyophilisation is carried out, for example, by filling a specific amount of the suspension into suitable dosage containers such as ampoules, e.g. vials, and subsequently freezing the vials at about −40° C. and then lyophilising the contents under a pressure of 0.2 to 0.6 mbar and at a final temperature of 25°–35° C.

The solid drug formulation so obtained, before it is used as suspension, for example before injection, is reconstituted in a physiological solution, e.g. a physiological sodium chloride solution, or a physiological sugar solution such as a glucose solution, or in distilled water. Brief shaking gives a homogeneous suspension which, by virtue of the phospholipid contained therein, does not adhere to the dosage container wall and can be removed readily and completely with a syringe.

Surprisingly, it is possible for the first time, by means of lyophilisation, to prepare solid drug formulations and suspensions which may be reconstituted therefrom that contain 4-hydroxy- or 4-acyloxy-4-androstene-3,17-diones, which suspensions are physically stable and are also suitable for injection. Accordingly, the invention also relates to stable injection suspensions which are used in particular as injection formulations. It is thus possible to use stable suspensions, in particular injection suspensions, that contain 4-hydroxy-or 4-acyloxy-4-androstene-3,17-diones, preferably 4-hydroxy-4-androstene-3,17-dione, as ready for use formulations.

The suspensions eligible for use as oral or injectable formulations may be administered orally or parenterally by methods known per se, as required together with other excipients, carriers and/or flavours and/or preservatives and/or antioxidants conventionally employed in galenic pharmacy.

From 10 to 1000 mg, preferably from 50 to 250 mg, of the compound of formula I

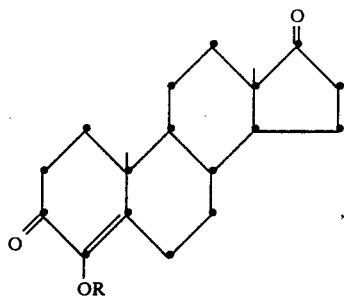

wherein R is a hydrogen atom or a $C_1$–$C_{12}$ acyl group, may be used for the preparation of the solid drug formulations and the suspensions which may be reconstituted therefrom and which are suitable for oral or injectable formulations.

Possible acyl groups are the acyl groups customarily employed in steroid chemistry, in particular the acetyl, heptanoyl or benzoyl group.

The compound of formula I will preferably be used in micronised form. If the drug is used in micronised form, the particles will have a particle size of 2–20 μm, but preferably an average particle size of 3–6 μm. Micronisation of the drug is effected with an ultrasonics disintegrator (e.g. Branson Sonifier) by known methods (J. Pharm. Sci., 53 (9), 1040–45 (1965).

Accordingly, the invention further relates to the compound of formula I in micronised form having a particle size of 2–20 μm, preferably an average particle size of 3–6 μm.

The compounds of the general formula I are known per se. They are described as inhibitors of aromatase which inhibit the conversion of 4-androstene-3,17-dione to oestrogen in human placental microsomes (Endocrinology 100 [1977], 1684–1695, and U.S. Pat. No. 4,235,893). The compounds are able to inhibit the development of oestrogen-dependent breast tumours in rats.

Further, the use of compounds of formula I for the prophylaxis and therapy of prostatic hyperplasia is disclosed in German Offenlegungsschrift 3 339 295.

The invention is illustrated by the following non-limitative Examples.

EXAMPLE 1

Composition of the dry vials:

| 4-hydroxy-4-androstene-3,17-dione, micronised | 250 mg |
|---|---|
| Epikuron 170 ® | 5 mg |
| Epikuron 200 ® | 45 mg |
| Carbowax 4000 ® | 150 mg |
| Thiomersal | 0.05 mg |

Preparation is effected with nitrogen blanketing and under aseptic conditions, 847.5 mg of sterile 4-hydroxy-4-androstene-3,17-dione are stirred into 6.407 g of filtered and sterilised suspension agent (17.0 mg of Epikuron 170 ®, 152.5 mg of Epikuron 200 ®, 508.5 mg of polyethylene glycol 4000 ®) to give a suspension. To this suspension are added 2.746 g of sterile filtered Thiomersal solution (0.170 mg of Thiomersal ®). The pH of the suspension is adjusted to 5.0–6.0 by addition of about 1 drop of sterile filtered 0.1 N sodium hydroxide solution. The suspension is homogenised (deagglomerated) with an ultrasonic disintegrator. 2.95 g of the suspension are filled into 6 ml vials. The contents of the vials are then frozen in a freeze-drying apparatus at −40° C. and subsequently lyophilised under a pressure of 0.4 mbar and a final temperature of +35° C.

Composition of the reconstituting medium:

| sodium chloride | | 18 mg |
|---|---|---|
| water | up to | 2 ml |

To prepare the ready for use suspension, 2 ml of 0.9% sodium chloride solution are added with an injection syringe to an ampoule containing lyophilised solid drug formulation. Brief shaking gives a homogeneous suspension which contains 250 mg of 4-hydroxy-4-androstene-3,17-dione.

EXAMPLE 2

Composition of the dry vial:

| 4-hydroxy-4-androstene-3,17-dione, micronised | 250.00 mg |
|---|---|
| Epikuron 200 ® | 50.00 mg |
| Carbowax 4000 ® | 75.00 mg |
| Thiomersal | 0.05 mg |
| ascorbyl palmitate | 0.005 mg |

Preparation is effected as described in Example 1 using the indicated amounts.

Composition of the reconstituting medium:

| water for injection | 2 ml |
|---|---|

EXAMPLE 3

Composition of the vial:

| 4-hydroxy-4-androstene-3,17-dione, micronised | 500 mg |
|---|---|
| Epikuron 170 ® | 50 mg |
| Polyglycol 3000 ® | 100 mg |
| Thiomersal | 0.05 mg |
| Tocopherol | 0.06 mg |

Preparation is effected as described in Example 1 using the indicated amounts.

Composition of the reconstituting medium:

| sodium chloride | | 22.5 ml |
|---|---|---|
| water for injection | up to | 2.5 ml |

EXAMPLE 4

Composition of the vial:

| 4-hydroxy-4-androstene-3,17-dione, micronised | 1000 mg |
|---|---|
| Epikuron 170 ® | 50 mg |
| Epikuron 200 ® | 50 mg |
| polyethylene glycol | 300 mg |
| Thiomersal | 0.05 mg |

-continued

| | |
|---|---|
| Tocopheral | 0.12 mg |

Preparation is effected as described in Example 1 using the indicated amounts.

Composition of the reconstituting medium:

| | | |
|---|---|---|
| glucose | | 250.0 mg |
| water for injection | up to | 5 ml |

EXAMPLE 5

Preparation of microcrystals:

250 mg of 4-hydroxy-4-androstene-3,17-dione are dissolved in 7.5 ml of acetone. This solution is mixed with 75 ml of water in an ultrasonic disintegrator. The precipitated microcrystals of 4-hydroxy-4-androstene-3,17-dione are collected on a filter by filtration and washed with two 10 ml portions of water. The washed microcrystals are dried at 40° C. and under a pressure of >100 mbar.

What is claimed is:

1. A solid drug formulation which is useful for the preparation of a stable suspension of said drug in a suspension vehicle, said formulation comprising
   (a) a micronized form of said drug which is selected from 4-hydroxy-4-androstene-3,17-dione and 4-acyloxy-4-androstene-3,17-dione and
   (b) a mixture of
      (i) at least one phospholipid and
      (ii) at least one polyethylene glycol,
      in a ratio i):ii) of 1:1 to 1:10,
   said (b) serving as a wetting agent and viscosity enhancing agent;
   said formulation being obtained by lyophilisation.

2. A solid drug formulation according to claim 1, which contains as wetting agent and as agent for raising the viscosity of the suspension vehicle a combination consisting of at least one phospholipid and at least one polyethylene glycol in the ratio of 1:1 to 1:5.

3. A solid drug formulation according to claim 1, which contains as wetting agent and as agent for raising the viscosity of the suspension vehicle a combination consisting of at least one phospholipid and at least one polyethylene glycol in the ratio of 1:1 to 1:3.

4. A solid drug formulation according to claim 1, wherein the polyethylene glycol is a solid polyethylene glycol.

5. A solid drug formulation according to claim 1, wherein the polyethylene glycol is a solid polyethylene glycol having a molecular weight of 1000 to 6000.

6. A solid drug formulation according to claim 1, which contains 4-hydroxy-4-androstene-3,17-dione, wherein the polyethylene glycol is a solid polyethylene glycol having a molecular weight of 3000 to 4000.

7. A stable suspension containing a solid drug formulation of the composition as claimed in claim 1, in an aqueous suspension vehicle.

8. A stable suspension according to claim 7 for oral or parenteral administration.

9. The formulation of claim 1 wherein said micronized particles are from 2 to 20 μm in size.

10. The formulation of claim 1 obtained by preparing a homogenous mixture of the ingredient in a vehicle and freeze-drying said mixture.

* * * * *